United States Patent [19]

Meckstroth

[11] Patent Number: 5,651,757

[45] Date of Patent: Jul. 29, 1997

[54] ENDOSCOPE WARMER

[76] Inventor: Clyde S. Meckstroth, 1081 New Parkview Pl., West Palm Beach, Fla. 33417

[21] Appl. No.: 601,741

[22] Filed: Feb. 15, 1996

[51] Int. Cl.$^6$ .................................................... A61B 1/06
[52] U.S. Cl. ..................... 600/169; 600/101; 600/133; 604/113
[58] Field of Search ........................ 600/101, 157, 600/158, 169, 133; 126/263; 604/291, 113, 206/219, 438; 601/151; 607/96, 104, 108

[56] References Cited

U.S. PATENT DOCUMENTS

| | | |
|---|---|---|
| 4,741,326 | 5/1988 | Sidall et al. . |
| 4,796,696 | 1/1989 | Stocton et al. .................. 604/113 X |
| 5,207,213 | 5/1993 | Auhll et al. . |
| 5,237,984 | 8/1993 | Williams, III et al. . |
| 5,250,032 | 10/1993 | Carter, Jr. et al. ..................... 604/113 |
| 5,295,964 | 3/1994 | Gauthier ................................ 604/113 |
| 5,313,934 | 5/1994 | Wiita et al. . |
| 5,351,675 | 10/1994 | Brodsky . |
| 5,392,766 | 2/1995 | Masterson et al. . |
| 5,400,767 | 3/1995 | Murdoch . |
| 5,411,541 | 5/1995 | Bell et al. .......................... 607/108 X |
| 5,413,092 | 5/1995 | Williams, III et al. . |
| 5,417,720 | 5/1995 | Mason ................................ 607/108 X |

FOREIGN PATENT DOCUMENTS 5-176887  7/1993  Japan ..................................... 600/133

*Primary Examiner*—Beverly M. Flanagan

[57] ABSTRACT

An endoscope warmer for preheating endoscopic surgical instruments, wherein the warmer comprises a holster, a plurality of channels formed in the wall of the holster for circulating a heated fluid, a supply port and a return port for maintaining a constant supply of heated fluid, and a pocket defined by the holster for receiving at least the optical shaft portion of the instrument and, in the alternative, the entire instrument. The supply and return ports are sealingly attached to the holster and are adaptable for connection to heating units and pumps for circulating the heated fluid through the holster.

21 Claims, 3 Drawing Sheets

ENDOSCOPE WARMER

BACKGROUND OF THE INVENTION

1. Field of the Invention

This invention relates generally to a device and method for preparing an endoscope instrument for use in medical procedures, and more particularly, to an apparatus and method for preheating an endoscope instrument, such as a laparoscope, thoracoscope, or arthroscope, prior to its use in a medical procedure.

2. Description of the Prior Art

Endoscopy is a surgical technique whereby a thin, fiber optic telescope (endoscope) is utilized to look inside the body cavity of a patient for diagnostic and therapeutic treatment. Examples of procedures that may be done endoscopically include laparoscopic cholecystectomies (gall bladder), laparoscopic appendectomies, laparoscopic colon resections, laparoscopic hernia repairs, laparoscopic hysterectomies, laparoscopic gynecological surgeries, and laparoscopic diskectomies. Other endoscopic techniques include arthroscopy, a procedure to diagnose and treat problems of the joints with a telescope, and thoracoscopy, a procedure for performing chest surgery with a telescope. As experience in the medical field increases, more of these types of procedures are being developed and accomplished with the endoscopic technique.

The first human endoscopic procedure was performed in 1910 by the Swedish physician Jacobaeus. Modern endoscopy procedures began in the early 1960s when the first fiber optic instruments were introduced. In the last ten years, endoscopy (laparoscopy, thoracoscopy, and arthroscopy) has come to the forefront of surgery with millions of these surgeries being performed each year. In fact, technological advances, such as computer aided video cameras and increasingly sophisticated endoscopic instrumentation, has revolutionized the field of surgery by allowing more procedures to be performed endoscopically. Despite its celebrated success, endoscopic surgery has been plagued with a persistent problem. Since its inception, the most common problem encountered in endoscopic surgery is fogging of the telescope lens. Although scope fogging ranks low in terms of severity on the overall scale of potential problems that can occur, it is still a nagging problem which occurs in almost all procedures. Fogging occurs when the endoscope, which is at room temperature (usually 70° to 80° F.) is introduced into the warm (98.6° F.), moist environment of the abdomen, joint space, or other body cavity. This problem is analogous to the fogging on a car window on a cold day or on a bathroom mirror during a shower.

Techniques for dealing with fogging have been around as long as the scopes, but no single answer has adequately addressed the problem. All attempts at prevention have been aimed at thwarting the basic environmental fact, i.e., a cold piece of glass placed in a wet, warm environment will fog. Methods commonly used to prevent endoscopic fogging have included warming the endoscope or chemically treating the endoscope lenses. An anti-fog chemical, such as Endo-Fog™ or F.R.E.D.™, has been used to chemically treat the endoscope lens prior to use to prevent fogging. Warming the endoscope has been done by wrapping it in a warm, moist towel or soaking it in warm saline prior to its use.

These anti-fogging methods, however, are unreliable. Anti-fog chemicals typically require several applications which necessitates removal from the body allowing the scope to cool. Using warm towels or saline solutions to prevent lens fogging is also undesirable. First, the towels rapidly cool down in the low temperature environment of the operating room. Second, in certain procedures, such as a cholecystectomy, the endoscope must be removed several times from the patient, so fresh, warm towels or saline solution must always be readily available. Third, warming solutions are often kept in a bowl-like dish which may easily be knocked over damaging the endoscope. Finally, it is difficult to maintain the scope at a constant temperature and to keep the endoscope sterilized with these noted warming procedures.

There is also a device known in the background art which provides a sheath as an alternative to warming an endoscope prior to use. However, this device does not adequately solve the above noted problems. Brodsky, in U.S. Pat. No. 5,351, 675, discloses a casing for preheating an optical instrument prior to use. The casing comprises an outer sleeve and an inner sleeve which includes first and second chemicals, respectively. These chemicals are mixable for producing an exothermic chemical reaction when disturbed in order to heat the sleeve and warm the laparoscopic instrument when it is received in the sleeve assembly. The heat is produced when a first envelope containing one of the chemicals is ruptured inside another envelope containing the other reactive chemical. The resulting chemical reaction produces the heat until the reaction is complete. This device is considered complicated in design, as it relies on an exothermic chemical reaction to produce heat. While this chemical reaction initially produces the necessary heat, the chemical reaction gradually subsides, especially in a lengthy surgical procedure, incrementally reducing in temperature until the sleeve is completely cooled. In addition, the chemical reaction can potentially harm a patient, cause some type of allergic reaction, burn the patient, or cause other side effects if the sleeve should leak.

Several other sheaths are contemplated in the background art, however, these sheaths do not address the concerns associated with lens fogging. Rather, they provide sheaths for insulating sterilized scopes or for cleaning the scope while it remains in the body. For example, U.S. Pat. Nos. 5,237,984 and 5,413,092, issued to Williams, III et al., and U.S. Pat. No. 4,741,326, issued to Sidall et al., provide a barrier between a non-sterile telescope and the patient's body cavity so as to eliminate the time consuming and expensive sterilization process required between uses of the endoscope. Plastic sheaths are disclosed in U.S. Pat. Nos. 5,207,213, issued to Auhil et al.; 5,313,934, issued to Wiita et al.; 5,400,767, issued to Murdoch; and 5,392,766, issued to Masterson et al., and comprise enclosures for telescopic instruments which facilitate in-the-body cleansing of a smudged lens, so that the scope may remain inside the patient.

The above-noted background art neither solves nor addresses the problems contemplated by the present invention. The devices known do not provide a warming device capable of controllably maintaining a constant temperature (body-like or otherwise) for an unlimited duration to prevent the well known problem of lens fogging associated with endoscopic surgery. In addition, some of the background devices can place the patient at risk of injury. Accordingly, there remains a need for a device capable of safely preheating an endoscopic instrument prior to use and heating it at intervals during its use so as to prevent lens fogging, a problem which has been around since the inception of endoscopic technology. The present invention solves these problems by providing an endoscope warming holster which conveniently, controllably and indefinitely maintains an endoscope at body temperature without the noted risk and drawbacks. While the endoscope warming holster is described in detail below with respect to endoscopes, the warming holster works for varying the temperature of any surgical instrument which requires preheating prior to use.

SUMMARY OF THE INVENTION

It is an object of the present invention to provide an endoscope warmer which can reliably prevent fogging of endoscope lenses without having to resort to an anti-fog chemical or placement in a warming solution or towel.

It is another object of the invention to provide an endoscope warmer that can elevate an endoscope to body temperature to eliminate temperature differentials in the body cavity so as to prevent lens fogging.

It is also an object of the invention to provide an endoscope warmer that is capable of maintaining a constant temperature.

It is an additional object of the invention to provide an endoscope warmer having adjustable temperatures.

It is a further object of the invention to keep an endoscope instrument sterilized.

It is yet another object of the instant invention to provide an endoscope warmer that is easily and inexpensively adaptable in current hospital operating rooms.

An additional object of the instant invention is to provide an endoscope warmer that provides a safe place to store an endoscope during waiting periods in surgery to protect the endoscope from damage while maintaining its body temperature.

A further object of the invention is to provide an endoscope warmer that is inexpensive to manufacture, easy to use, and safe for the patient.

In accordance with these and other objects, the endoscope warmer of the instant invention comprises a holster formed by at least one tubular, elongated, flexible wall and having at least one open end defining a scope-receiving pocket for inserting the endoscope. The wall preferably comprises a heating pad structure well known in the medical field (commonly referred to as a K-pad) comprising plastic or plastic-like thermal insulate material defining a plurality of channels formed in the structure for circulating a warm fluid through the pad. The opposing side edges of the pad are sealingly joined by a fusion, adhesion or similar process to construct a substantially tubular, elongated, flexible holster, leaving one end open to receive the scope instrument for insulation.

The instant invention preferably includes a plurality of channels formed in the walls of the holster for passing a warm fluid through the pad. The fluid may be a water or water-based fluid and is preferably warmed to body temperature (98.6° F.). The channel receives the warm fluid from a supply port, passes the fluid through the pad walls, and outputs the fluid through a return port. The supply and return ports comprise additional flexible, plastic tubes adapted for sealed attachment in the wall of the pad in fluid communication with the channels.

The fluid may be warmed and circulated through the pad with a heating unit/pump currently in existence in most medical facilities. The heating unit preferred is temperature adjustable and must be capable of being set to temperatures that warm the fluid to body temperatures. The heating unit maintains the fluid at the desired temperature through the holster channels so that a warm fluid at a constant temperature is always available. Consequently, the holster can be sustained at the elevated temperature until surgery is complete without interrupting surgery. By passing the heated fluid through the pad, the holster is heated and transfers the heat to the endoscope while it rests in the holster pocket until it's temperature is elevated to the desired level. The temperature of the pad may be raised above body temperature to expedite the heating of the scope and account for heat loss. A thermostat may be used to determine when the scope instrument reaches the requisite temperature. By bringing the endoscope to body temperature, temperature differentials between the instrument and body cavity are eliminated so as to prevent any fogging of the lens.

The instant invention provides several advantages over the background art. The endoscope warming holster may be constructed from an existing and widely accepted heating pad in the medical community. The heating pad employed may include a commonly used product known in the industry as a "K-pad." However, other pads, plastic sheets and materials may be employed without departing from the scope of the instant invention so long as channels can be formed within its structure and it can be sealed at its edges. The endoscope warmer may be easily and inexpensively manufactured. In contrast with the background devices, the warming holster maintains its temperature by circulating an externally heated fluid through the pad at a controlled rate. The temperature is also variable via the adjustment of a heat unit setting. Consequently, the endoscope may be placed into the holster prior to surgery and during surgery to prevent cooling outside the body, as is common in devices incapable of sustaining a raised temperature. In addition, the endoscope holster provides a protective shell when filled with fluid for storing the endoscope instrument and insulating it from damage before, during, and after surgery.

In accordance with these and other objects which will become apparent hereinafter, the instant invention will now be described with particular reference to the accompanying drawings.

BRIEF DESCRIPTION OF THE DRAWINGS

The invention is described in detail below with reference to the accompanying drawings, in which.

DESCRIPTION OF THE PREFERRED EMBODIMENTS

Figure 1:
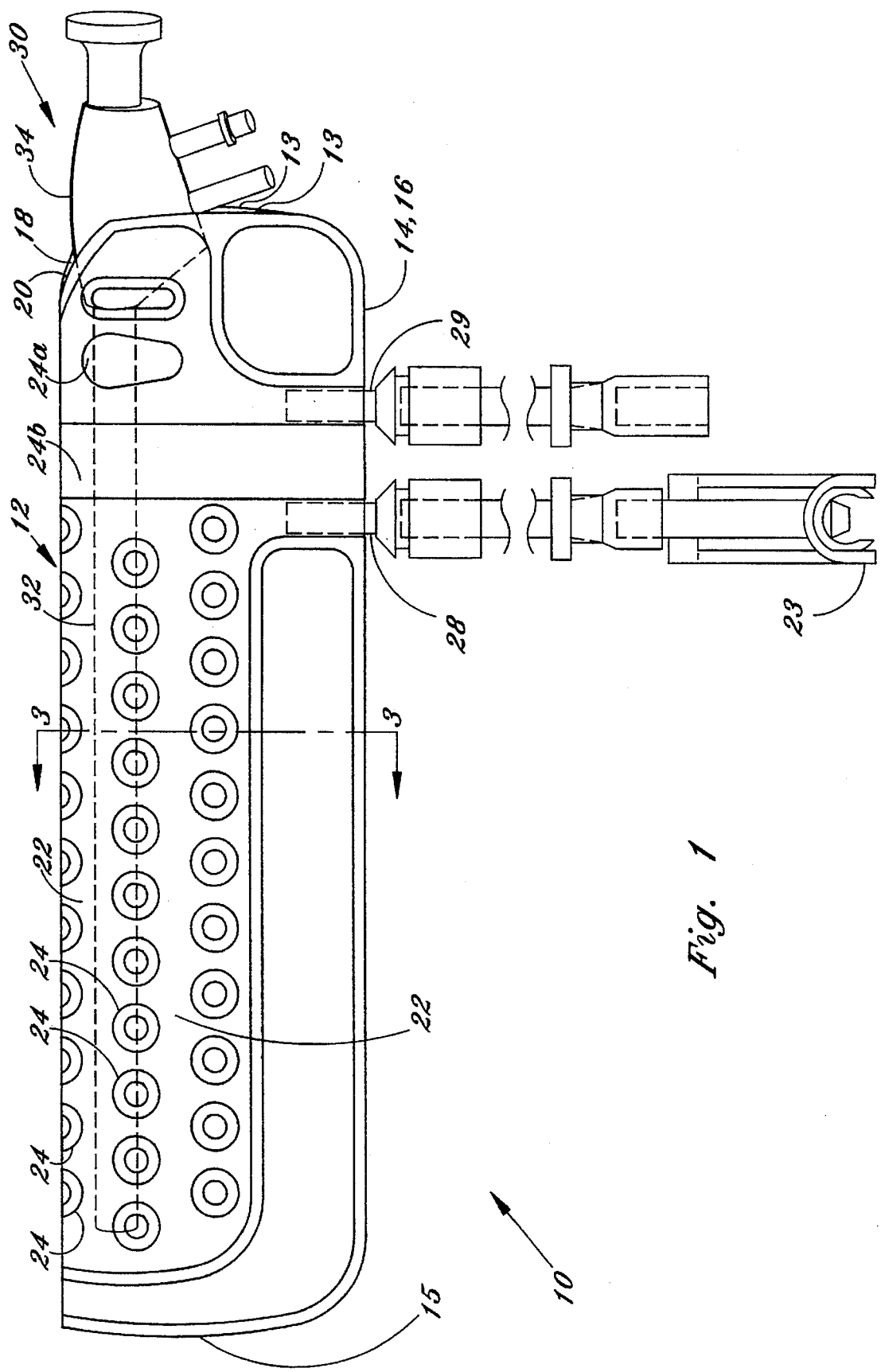
FIG. 1 is a perspective view of the preferred embodiment of the endoscope warmer of the instant invention showing the endoscope in phantom inserted into the warmer and further illustrating the supply and return port hoses.
Figure 2:
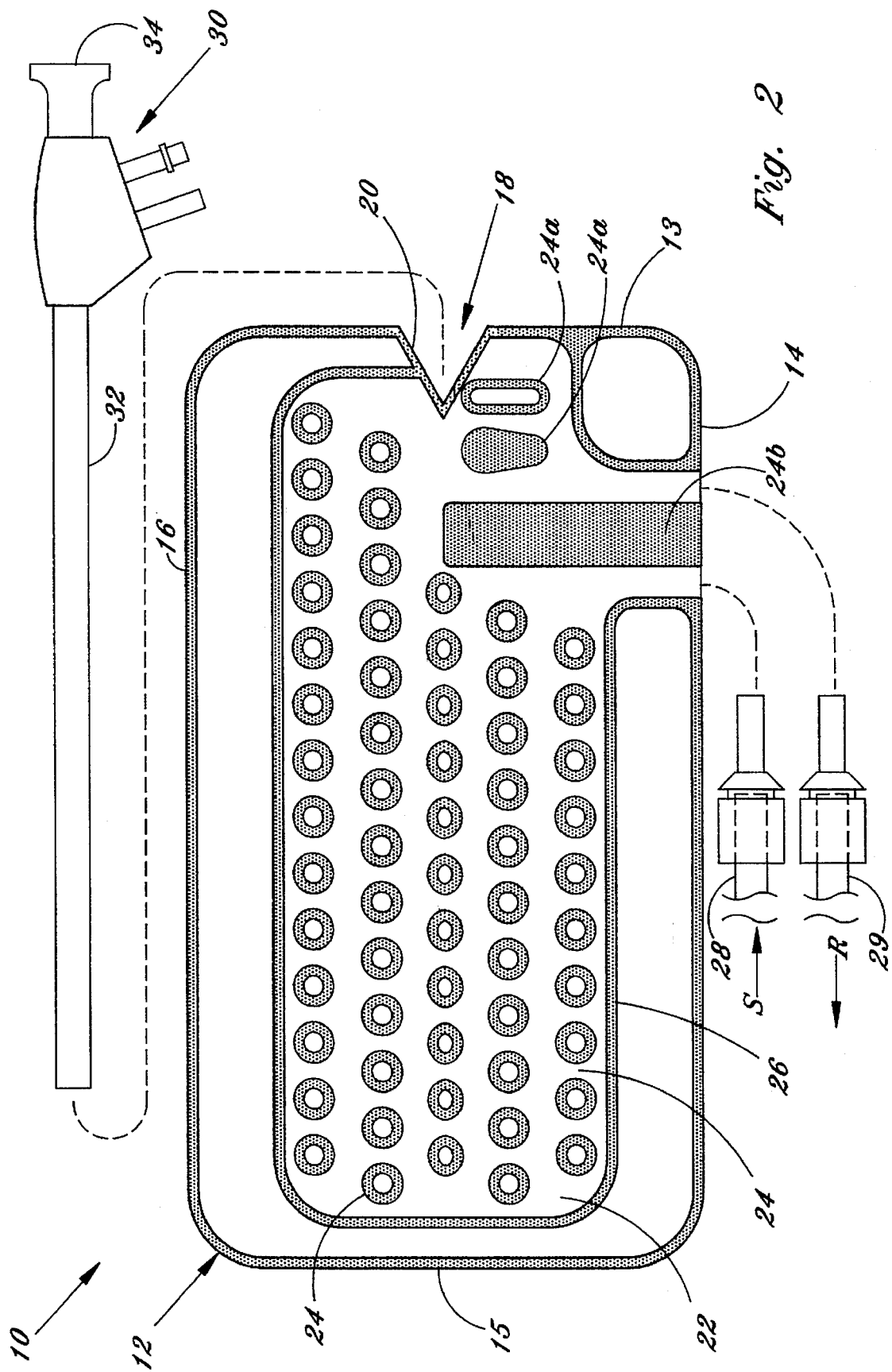
FIG. 2 is a plan exploded view of the preferred embodiment of the heat pad used to construct the endoscope warmer, illustrating the endoscope and hoses exploded from the pad.
Figure 3:
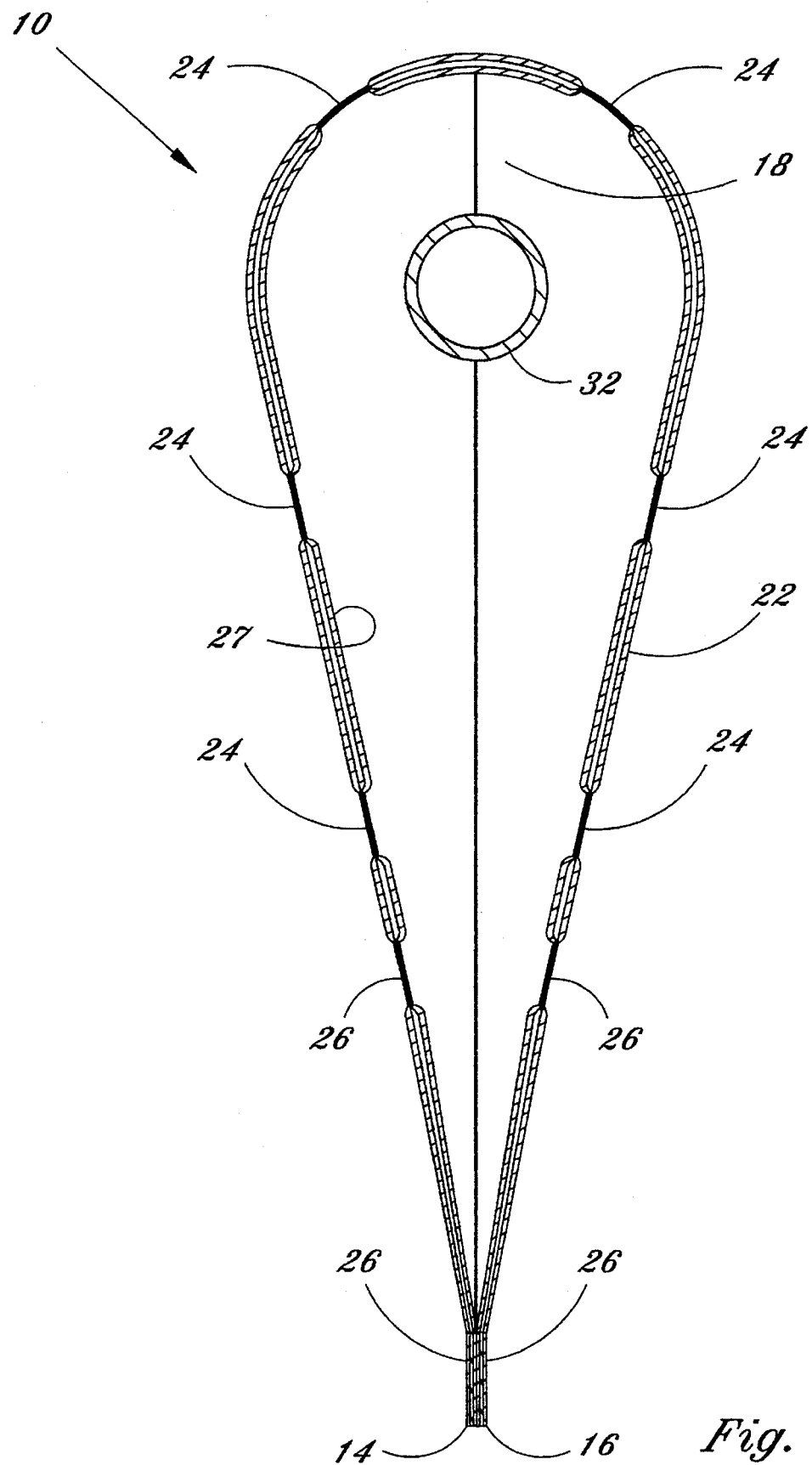
FIG. 3 is a cross sectional view taken along lines 3—3 of FIG. 1, illustrating the channels formed in the holster walls.

With reference to the drawings, FIGS. 1–3 show the preferred embodiment of the endoscope warmer 10 of the instant invention, preferably for use with a scope instrument having an elongated optical shaft 32 and base 34. The instant invention may also be employed with other surgical instruments requiring preheating before use. The endoscope warmer 10 generally comprises a substantially tubular, elongated and flexible holster or sleeve 10, an endoscope receiving passage 18 defined by the holster 10, a plurality of channels 22 formed in the walls of the holster 10, and a means for circulating a heated fluid through the channels 22 which includes an input port 28 and a return port 29 fluidly connected to a heating unit/pump (not shown). The holster 10 may be other than tubular without departing from the scope and spirit of the invention.

The fluid employed is preferably a sterilized water, water solution, or other liquid which is easily heated to body temperature and safe for the patient. The heating unit and/or pump (hereinafter "heat pump") may be any device known in the art and/or currently used by hospital practitioners. The instant invention is intended to be adaptable for connection to heat pumps currently in use in hospitals to reduce the capital outlay required for adopting the endoscope warmer 10.

Referring to FIG. 1, the holster 10 comprises a plastic pad 12 folded over itself and sealed along its edges to create a substantially tubular holster or sleeve 10 having at least one open input end 13. The holster 10 is preferably elongated and flexible for accommodating endoscopic instruments 30 having an elongated optical shaft 32, as shown in FIG. 1. A pliable plastic pad 12 capable of expansion under the pressure of a flowing fluid and the retention of heat is also preferred. The plastic pad 12 should be medically safe such as the K-pad currently employed by the medical community and depicted in the drawings.

With reference to FIG. 1, the holster 10 is sealed along its distal edge 15, and side edges 14 and 16, leaving the input end 13 open for receiving the scope instrument 30. The edges 14, 15, 16, and the lower part of the open end 13 may be sealed by fusing, heat curing, adhesives, or other known methods for sealingly joining plastic sheets. The edges are sealed to define the pocket 18, the volume of which may be reduced by adjusting the lines of adhesion 26. The reference numeral 26 illustrates the locations where the holster 12 is sealed. Thus, as shown in FIG. 1., the holster 10 can define a smaller pocket 18 by sealing the pad 12 proximal the area forming channels 22 or a larger volume by sealing along the peripheral edges 13–16. A smaller pocket 18 may be preferred for accommodating the optical shaft 32 so as to have a smaller volume to heat and a more closed-in area for containing and more efficiently heating the endoscope shaft 32. The panel edges may also be joined so as to have a volume gradient along the holster 10 or to create a open end 13 having a larger cross section than the pocket 18 cross section to receive the entire instrument 30, including its base 34. In the alternative, the pocket 18 may be formed by merely joining the side edges 14 and 16, leaving two open ends for inserting the endoscope.

With reference to FIGS. 1 and 2, the pad 12 may be any pad known in the art, such as the "K-pad." The pad 12 is formed by joining two plastic, plastic-like, or similar thermal, medically safe sheets 12a and 12b along their edges 13–16 and at selected locations around its midsection. The first and second sheets 12a, 12b comprise an inner wall and outer wall which are joined by any commonly accepted practice, such as fusing, heat curing, adhesives, or other similar method.

While the wall of the instant invention may incorporate a known pad having a supply and return port 28, 29 for interfacing with a fluid heat pump, the invention modifies the pad by folding it into a "holster" or pocket to receive, surround and warm an endoscope instrument. The orientation of the supply port 28 and return port 29 may vary without departing from the scope and spirit of the instant invention so long as adequate circulation is provided. Flexible conduit lines in the form of a supply tube 28 and return tube 29 are sealingly secured between the pad sheets 12a, 12b when the pad sheets 12a, 12b are adhered or joined together to define the input and output ports. These tubes 28, 29 extend from the holster 10 and sealingly attach to the heat pump. The supply and return lines 28, 29 may be known by practiced artisans and may include connectors that are adaptable for connection to the heat pump.

Circulation of the heated fluid through the channels 22 is effected by the heat pump. The channels 22 are defined by a plurality of barriers 24 formed when the first and second sheets 12a, 12b are joined, by adhesion, fusion or other similar processes, at select positions leaving continuous void passages throughout the pad 12. Accordingly, the channels are defined by the free space left between the sheets 12a, 12b. The circulation of fluid through the channels is further dictated by the spatial relationship between barriers 24. An elongated barrier 24b is also formed between the supply port 28 and return port 29 to more distinctly define a supply and return path as shown in FIG. 2. Larger barriers, such as 24a and 24b, may also be formed by the same methods noted herein to control the flow of fluid through the channels as desired. It should be noted that the barriers 24, 24a, and 24b may vary in size and spatial relationship without departing from the scope and spirit of the instant invention. It is the intention of the instant invention to circulate the fluid at a rate which affords efficient use of energy for maintaining the holster 10 at its desired temperature.

The holster 10 may include a cutout 20 at the input end 13 of the holster for allowing deeper penetration of the endoscope instrument 30 into the pocket/passage 18. This also has the benefit of closing off the input end 13 to prevent heat loss from the holster pocket 18. The opening at the input end 13 may also be larger than the opening defined by pocket 18 for facilitating full receipt of the endoscope during preheating.

Referring to FIG. 3, the holster 10 is shown in cross section to illustrate the channels 22, the fusing of the pad sheets 12a, 12b, and the liner 27. The channels 22, as illustrated in FIG. 3, depict the separation between the first pad sheet 12a and second pad sheet 12b as occurs when water is being circulated through the holster 10. The channels 22 are formed by fusing the first and second pad sheets 12a, 12b at a plurality of selected points 24 defining the channel barriers 24. As noted above, the sheets 12a, 12b may be fused together by any known adhesion process. A liner 27 may also be adhered along the interior wall, i.e. the first sheet 12a, in the pocket 18 to provide insulation and reduce heat loss. The liner 27 may comprise an insulating material, cloth, flannel or other thermal material.

The instant invention avoids the use of special chemicals which have been used in the past for eliminating lens fogging and creating chemical reactions in producing heat. Rather, the instant invention employs heat units/pumps currently known in the art for connection to the supply port 28 and return port 29 to effectuate a flow of heated fluid through the holster channels 22. The instant invention is intended to be adaptable for connection to existing heat pumps facilitating convenient and instant operability. The instant invention may also be employable for other medical instruments that necessitate preheating prior to use. An endoscope 30 is shown by way of illustrating the use of the instant holster 10 in its preferred embodiment. The endoscope selected includes an optical shaft portion 32 which is received by the holster pocket/passage 18 for warming. The pocket 18 may be sized for only receiving the optical shaft 32 or it may include an enlarged opening at the input end 13 for receiving the entire instrument 30. The instant invention may be made by clear plastic or an opaque plastic without departing from the objectives of the instant invention.

Although several preferred embodiments of the invention have been described in detail herein for illustrative purposes, it will be appreciated by those skilled in the art that many additions, modifications, and/or substitutions may be made without departing from the spirit and scope of the invention as defined in the accompanying drawings.

What I claim is:

1. A surgical scope warming holster for preheating and heating a surgical scope before and during surgery, respectively, the surgical scope having an elongated optical shaft, said holster comprising:

an elongated sleeve constructed by a flexible wall, said sleeve having at least one open end for receiving the scope, said sleeve defining a pocket in communication with said open end and sized for storing at least the surgical scope optical shaft, said open end defining an opening having a cross section exceeding a cross section of said pocket;

a plurality of channels formed in said wall for circulating a heated fluid through said wall to heat said sleeve and the scope while the scope is stored in said pocket;

said wall comprising an inner wall and an outer wall attached at a plurality of select locations so as to create a plurality of barriers therebetween, thereby forming said channels, said channels defined by voids remaining between said inner wall and said outer wall;

a supply port sealingly attached to said wall in fluid communication with said channels, said supply port for supplying a heated fluid to said channels, said supply port adaptable for receiving the heated fluid from an exterior source;

a return port in fluid communication with said channels for returning the heated fluid to the exterior source, said wall separating said supply port and said return port so as to allow flow of the heated fluid through said channels;

an elongated flow barrier extending into said wall and separating said supply port from said return port, said outer wall and said inner wall attached along said elongated flow barrier to form said flow barrier therebetween; and a thermal liner lining said inner wall inside said pocket for reducing heat loss from said pocket.

2. A holster as recited in claim 1, further comprising:

a cutout defined by said sleeve for receiving the entire surgical scope.

3. A holster as recited in claim 1, wherein said inner wall and said outer wall are fused together along their edges, along said elongated flow barrier, and at said select locations.

4. A holster as recited in claim 1, wherein said sleeve is fabricated from a medically safe plastic.

5. A holster as recited in claim 1, wherein said sleeve provides a protective cushion when filled with the fluid for insulating the surgical scope from impact damage.

6. A holster as recited in claim 1, wherein said supply port comprises a first flexible conduit and said return port comprises a second flexible conduit.

7. A holster as recited in claim 1, further comprising a means for heating the fluid, said heating means in fluid communication with said supply port and said return port.

8. A surgical instrument warming holster for preheating and heating a surgical instrument before and during surgery, respectively, said holster comprising:

an elongated sleeve comprising a flexible wall having an inner wall and an outer wall attached along its edges, said flexible wall having a first side edge and a second side edge joined to form said sleeve such that said sleeve has at least one open end for receiving the scope, said sleeve defining a pocket in communication with said open end and sized for storing the surgical instrument, said sleeve defining a cutout for receiving the entire surgical scope;

a plurality of channels formed by said inner wall and said outer wall, between said inner wall and said outer wall, for circulating a heated fluid through said wall to heat said sleeve and the scope while the scope is stored in said pocket, said inner wall and said outer wall being attached at a plurality of select locations so as to form said channels, said channels defined by voids remaining between said inner wall and said outer wall;

a supply port sealingly attached to said wall in fluid communication with said channels, said supply port for supplying a heated fluid to said channels, said supply port adaptable for connection to an exterior heated fluid source for receiving the heated fluid from the exterior heated fluid source;

a return port in fluid communication with said channels, said return port adaptable for connection to the exterior heated fluid source for returning the heated fluid to the exterior heated fluid source, said wall separating said supply port and said return port so as to allow flow of the heated fluid through said channels;

an elongated flow barrier extending into said wall and separating said supply port from said return port, said outer wall and said inner wall attached along said elongated flow barrier to form said flow barrier therebetween; and a thermal liner lining said inner wall inside said pocket for reducing heat loss from said pocket.

9. A holster as recited in claim 8, wherein said open end defines an opening having a cross section exceeding a cross section of said pocket.

10. A holster as recited in claim 8, wherein said inner wall and said outer wall are fused together along their edges, along said elongated flow barrier, and at said select locations.

11. A holster as recited in claim 8, wherein said sleeve is fabricated from a medically safe plastic.

12. A holster as recited in claim 8, wherein said supply port comprises a first flexible conduit and said return port comprises a second flexible conduit.

13. A holster as recited in claim 8, further comprising a means for heating the fluid, said heating means in fluid communication with said supply port and said return port.

14. A surgical scope warming holster for preheating and heating a surgical scope before and during surgery, respectively, the surgical scope having an elongated optical shaft, said holster comprising:

an elongated sleeve constructed by a flexible wall, said sleeve being joined along selected edges so as to define a holster having at least one open end for receiving the scope in said holster, said holster having a volume sized for surrounding and storing at least the surgical scope optical shaft;

a plurality of channels formed in said wall for circulating a heated fluid through said wall to heat said sleeve and the scope while the scope is stored in said pocket;

a supply port sealingly attached to said wall in fluid communication with said channels, said supply port for supplying a heated fluid to said channels, said supply port adaptable for receiving the heated fluid from an exterior source; and a return port in fluid communication with said channels for returning the heated fluid to the exterior source, said wall separating said supply port and said return port so as to allow flow of the heated fluid through said channels.

15. A holster as recited in claim 14, wherein said wall comprises an inner sheet and an outer sheet, said inner sheet and said outer sheet being attached at a plurality of select locations so as to form said channels, said channels being defined by voids remaining between said inner sheet and said outer sheet.

16. A holster as recited in claim 15, further comprising:

an elongated flow barrier extending into said wall and separating said supply port from said return port, said outer sheet and said inner sheet being attached along said elongated flow barrier to form said flow barrier therebetween.

17. A holster as recited in claim 16, further comprising:

a thermal liner lining said inner sheet inside said holster volume for reducing heat loss from said pocket.

18. A holster as recited in claim 17, wherein said open end defines an opening having a cross section exceeding a cross section of said holster.

19. A holster as recited in claim 16, wherein said inner sheet and said outer sheet are fused together along its edges, along said elongated flow barrier, and at said select locations.

20. A holster as recited in claim 16, wherein said supply port comprises a first flexible conduit and said return port comprises a second flexible conduit.

21. A holster as recited in claim 16, further comprising a means for heating the fluid, said heating means in fluid communication with said supply port and said return port.

* * * * *